US00PP20348P2

(12) United States Plant Patent
Vergeldt

(10) Patent No.: US PP20,348 P2
(45) Date of Patent: Sep. 22, 2009

(54) *MISCANTHUS* PLANT NAMED 'LOTTUM'

(50) Latin Name: *Miscanthus giganteus*
Varietal Denomination: Lottum

(76) Inventor: Jozef H. Vergeldt, Pastoor Kerboschlaan 10, Lottum, NV (NL) 5973

( * ) Notice: Subject to any disclaimer, the term of this patent is extended or adjusted under 35 U.S.C. 154(b) by 0 days.

(21) Appl. No.: 12/079,637

(22) Filed: Mar. 27, 2008

(51) Int. Cl.
*A01H 5/00* (2006.01)

(52) U.S. Cl. ..... Plt./384

(58) Field of Classification Search ..... Plt./384
See application file for complete search history.

(56) References Cited

OTHER PUBLICATIONS

UPOV Plant Variety Database search for PBR 20061707 2006 cultivar Lottum. 1 page.*

* cited by examiner

*Primary Examiner*—Annette H Para

(57) ABSTRACT

A new and distinct *Miscanthus* cultivar named 'Lottum' is disclosed, characterized by rapid, vigorous growth, and long, green leaves, marked with golden yellow blotches.

1 Drawing Sheet

Figure 1:
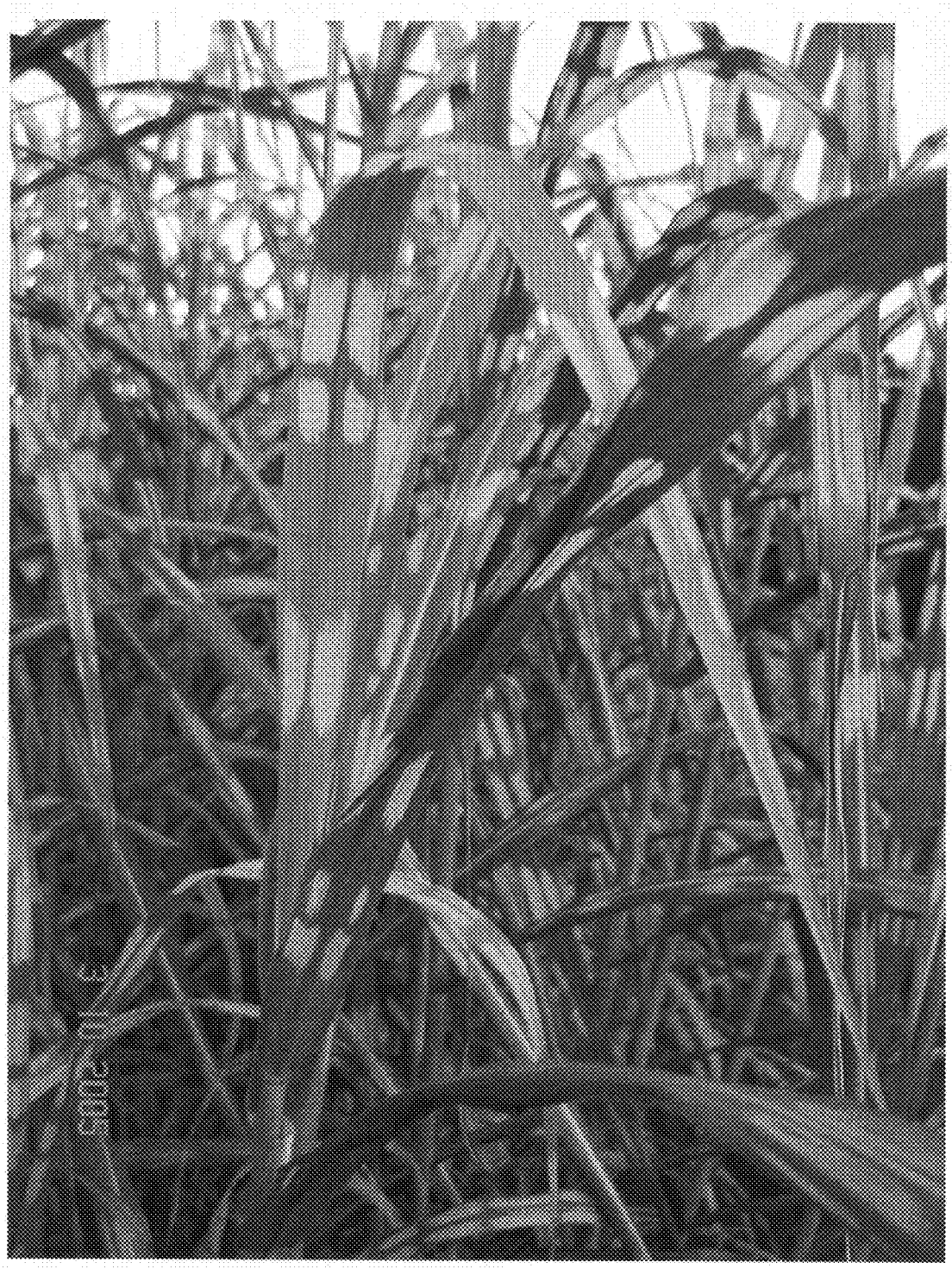

Latin name of the genus and species: *Miscanthus giganteus.*

Variety denomination: 'Lottum'.

BACKGROUND OF THE INVENTION

The new cultivar was discovered by the inventor, Johannes Vergeldt, a citizen of the Netherlands in July of 1999 as a naturally occurring, whole plant mutation in a commercial nursery in Lottum, the Netherlands. The parent variety is an unnamed variety of *Miscanthus giganteus.*

Asexual reproduction of the new cultivar 'Lottum' was first performed in Lottum, the Netherlands by vegetative division in June 2006. Subsequently, at least 6 generations of 'Lottum' have been reproduced and have shown that the unique features of this cultivar are stable and reproduced true to type.

SUMMARY OF THE INVENTION

The cultivar 'Lottum' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Lottum' These characteristics in combination distinguish 'Lottum' as a new and distinct *Miscanthus* cultivar:

1. Fast growth habit, reaching a height of at least 2 meters in one growing season, in the Netherlands.
2. Distinctive yellow blotches over green foliage.
3. Very long leaves, at least 1 meter longer than comparable yellow and green varieties.

COMPARISON TO PARENT

Plants of the new cultivar 'Lottum' are similar to plants of the parent variety *Miscanthus giganteus* in most horticultural characteristics, however, 'Lottum' has distinctive yellow and green foliage while the parent variety produces only green foliage.

COMMERCIAL COMPARISON

Plants of the new cultivar 'Lottum' can be compared to the commercial variety *Miscanthus sinensus* 'Zebrinus,' unpatented. Plants of the 'Zebrinus' have a similar foliage coloration. However, plants of the new cultivar 'Lottum' grow to 2 meters in height, whereas plants of 'Zebrinus' only grow to 1 meter high.

BRIEF DESCRIPTION OF THE PHOTOGRAPH

The accompanying photograph in FIG. 1 illustrates in full color a typical plant of 'Lottum' grown outdoors in Lottum, the Netherlands. This plant is approximately 2 years old, shown growing in the ground. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Lottum' plants grown outdoors in the Netherlands. Temperatures ranged from 0° C. to 9° C. at night to 7° C. to 13° C. during the day. No artificial light, photoperiodic treatments or chemical treatments were given to the plants. Measurements and numerical values represent averages of typical plant types.

Botanical classification: *Miscanthus giganteus* 'Lottum.'

PLANT

Growth habit: Upright, perennial grass, forming long, arching leaves

Plant shape: Inverted triangle.

Height: Approximately 132.8 cm.

Plant spread: Approximately 77 cm.

Growth rate: Rapid, approximately 25 cm per month.

Branching characteristics: Herbaceous shoots emerging basally.
Number of shoots per plant: Approximately 10.
Average length of shoot: 78.1 cm.
Average width of shoot: 0.5 cm
Age of plant described: Approximately 2 years.
Internode length: Average 9.1 cm.
Texture of shoots: Smooth, non-pubescent.
Stem strength: Very strong.
Stem color: Near RHS Yellow-Green 144B.
Roots: Moderately dense, fine, slightly fibrous root color near RHS 156 A/D.

FOLIAGE

Leaf:
*Arrangement.*—Alternate.
*Compound or single.*—Single.
*Quantity of leaves per shoot.*—14.
*Average length, excluding sheath.*—Approximately 52.6 cm.
*Average width.*—Approximately 1.4 cm.
*Average length of sheath.*—13.1 cm.
*Shape of blade.*—Linear.
*Aspect*—Arching.
*Apex.*—Long acuminate.
*Base.*—Cuneate, leaves sheathing.
*Margin.*—Smooth, but very sharp when rubbed downwards; due to very small, very sharp teeth (average: 30 teeth/cm).
*Texture of top surface.*—Smooth, slightly glossy.
*Texture of bottom surface.*—Smooth, moderately glossy.
*Pubescence.*—Margins of sheaths densely pubescent at first, when leaves mature the sheaths become glabrous, average length of hairs 2.5 mm, colored near RHS Greyed-White 156D.
*Color.*—Young foliage upper side: Near R.H.S. Green; 143 A and 143 B, with horizontal bands colored Yellow-Green; 145A; Base yellow-green; 144A. Young foliage under side: Near R.H.S. Green; 143 A and 143 B, with horizontal bands colored yellow-green; 145A. Base yellow-green; 144C. Mature foliage upper side: Near R.H.S. Green; Between 137A and 137B, with horizontal bands colored between yellow-green; 150B and 151D. Base green; 137B and C. Mature foliage under side: Near R.H.S. Green; 137B, with horizontal bands colored yellow-green; 151C and 151D. Base green; 137C.
*Venation.*—Type: Parallel. Venation coloration upper side: Near RHS Greyed-White; 156D Venation coloration under side: Near RHS Green; 137B.
Petiole: Not present, leaves sheathing.
*Sheath color.*—Near RHS Green 137C.

INFLORESCENCE Flowering has not been observed to date and is not commercially important in this cultivar.

OTHER CHARACTERISTICS

Disease resistance: Neither resistance nor susceptibility to diseases or pests has been observed in this variety.
Drought tolerance and cold tolerance: Observed to tolerate temperatures to 35° C. without any negative effects. Temperature tolerance above this range has not been observed. Tolerance of cold temperatures to at least USDA zone 6.
Fruit/seed production: Not observed.

What is claimed is:

1. A new and distinct cultivar of *Miscanthus* plant named 'Lottum' as herein illustrated and described.

* * * * *